US007919443B2

(12) United States Patent
Domaradzki

(10) Patent No.: US 7,919,443 B2
(45) Date of Patent: Apr. 5, 2011

(54) EXFOLIATING SCRUB BAR

(76) Inventor: Irena Anna Domaradzki, Olmsted Falls, OH (US)

( * ) Notice: Subject to any disclaimer, the term of this patent is extended or adjusted under 35 U.S.C. 154(b) by 261 days.

(21) Appl. No.: 12/287,680

(22) Filed: Oct. 14, 2008

(65) Prior Publication Data

US 2009/0111725 A1 Apr. 30, 2009

Related U.S. Application Data

(60) Provisional application No. 61/000,694, filed on Oct. 29, 2007.

(51) Int. Cl.
*A61K 7/50* (2006.01)

(52) U.S. Cl. ......................... 510/141; 510/146; 510/152

(58) Field of Classification Search ........................ None
See application file for complete search history.

(56) References Cited

U.S. PATENT DOCUMENTS 6,730,642 B1 * 5/2004 Aronson et al. .............. 510/146

* cited by examiner

*Primary Examiner* — Necholus Ogden, Jr.

(57) ABSTRACT

An exfoliating scrub bar for various parts of the body is made from natural ingredients that exfoliate the skin gently and effectively. The scrub bar comprises powdered or crushed nuts; powdered or crushed oats; and glycerin. The combination of ingredients allows a person to gently exfoliate different parts of the body depending on the location and/or skin sensitivity. The scrub bar provides the user with an effective tool for exfoliation that allows for the removal of dead skin cells.

8 Claims, 1 Drawing Sheet

EXFOLIATING SCRUB BAR

The present application claims priority to U.S. Provisional Patent Application Ser. No. 61/000,694, entitled NUTT SO RUFF SCRUB BAR and filed on Oct. 29, 2007. The disclosure of that application is hereby fully incorporated by reference herein.

BACKGROUND

The present disclosure relates to exfoliating products that are used to exfoliate various parts of the body.

Exfoliation is a process in which the surface layer of dead skin cells is removed. While the skin will exfoliate on its own, manual exfoliation removes dead skin cells and increases circulation. The result is softer, smoother, healthier glowing skin. Exfoliation is especially helpful for oily skin because oil clogs skin pores, which could cause unsightly acne blackheads. Exfoliation also helps dry skin, which otherwise tends to look dull. Because dead skin cells generally accumulate faster than natural exfoliation, the skin's natural exfoliating ability and moisture absorption ability are inhibited. Regular exfoliation thus allows the skin to absorb more moisture, reduce fine lines from wrinkles, and decrease acne.

Traditional means of exfoliation include using pumice stones, corn/callus removers, chemical peels, and facials. Pumice stones operate as an abrasive, and therefore do not provide gentle skin exfoliation. Corn/callus removers typically include a sharp blade, which can be dangerous if improperly used. Such situations are common because corn/callus removers are typically used with running water, such as in a sink or during a shower. Wet hands increase the chance that the remover will slip from the hand and cause cuts. Chemical peels and facials can be expensive. Patients can also have severe skin reactions, such as breakouts and skin redness.

There are some over-the-counter products that attempt to aid exfoliation as well. Many of these products come in the form of gels or pastes. As a result they can be messy to use. Some of these over-the-counter products can also be harsh to sensitive skin. In addition, gels and pastes are hard to use without making a mess, and are especially difficult to use in the shower.

It would be desirable to provide an exfoliation product that can be used on various parts of the body, depending on skin sensitivity, and can be used on a daily basis if desired. Such a product should also be effective at removing dead skin, but gentle on the skin.

BRIEF DESCRIPTION

Disclosed in various embodiments is a scrub bar that uses natural ingredients to exfoliate the skin gently and effectively. The bar form allows a person to use the scrub bar in the shower and easily cleanse themselves.

Disclosed in embodiments is a scrub bar comprising three ingredients: powdered or crushed nuts; powdered or crushed oats; and glycerin. In some embodiments, the scrub bar consists of the nuts, oats, and glycerin.

In particular embodiments, the nuts comprise from about 6 to about 12.5 weight percent of the scrub bar. The oats may also comprise from about 6 to about 12.5 weight percent of such embodiments.

In other embodiments, the oats comprise from about 6 to about 12.5 weight percent of the scrub bar.

In some embodiments, the nuts comprise about 6.25 weight percent of the scrub bar and the oats comprise about 6.25 weight percent of the scrub bar. In additional embodiments, the nuts comprise about 9.375 weight percent of the scrub bar and the oats comprise about 9.375 weight percent of the scrub bar. In yet other embodiments, the nuts comprise about 10 weight percent of the scrub bar and the oats comprise about 10 weight percent of the scrub bar.

The glycerin may comprise from about 75 to about 88 weight percent of the scrub bar.

Desirably, the nuts and oats have a particle size of 1 mm or less. Preferably, the nuts used in the scrub bar are almonds.

The scrub bar may not contain animal fats or oils, methyl alcohol or ethyl alcohol, a colorant, or an odorant.

Sometimes, the oats and nuts are evenly dispersed throughout the glycerin. However, the oats and nuts may also be preferentially located near a surface of the scrub bar.

Disclosed in other embodiments is a scrub bar comprising: from about 6 to about 12.5 weight percent of powdered or crushed nuts; from about 6 to about 12.5 weight percent of powdered or crushed oats; and from about 75 to about 88 weight percent of glycerin; wherein the weight ratio of nuts to oats is about 1:1.

Also disclosed is a method for producing a scrub bar. Liquid glycerin is provided in a container. The powdered or crushed nuts and oats are added to the liquid glycerin. The liquid glycerin is mixed to disperse the nuts and oats, thereby forming a mixture. The mixture is poured into a mold and cooled to form the scrub bar.

These and other non-limiting characteristics of the present disclosure are more particularly described below.

DETAILED DESCRIPTION

The scrub bar of the present disclosure comprises (a) powdered or crushed nuts; (b) powdered or crushed oats; and (c) glycerin. In some embodiments, the scrub bar consists of the nuts, oats, and glycerin only.

In embodiments, the powdered or crushed nuts are each present in the amount of from about 6 to about 12.5 weight percent of the scrub bar. The term "nut" refers generally to a kernel found within a shell or husk. Although any nut can be used, generally peanuts are avoided due to peanut allergies amongst the general population. Desirably, crushed or powdered almonds are used. Other nuts which may be useful in the scrub bar of the present disclosure include almonds, walnuts, chestnuts, pecans, cashews, macadamia nuts, and pistachios.

In embodiments, the powdered or crushed oats are each present in the amount of from about 6 to about 12.5 weight percent of the scrub bar.

The nuts and oats are powdered or crushed. In other words, they are processed from their original intact state into a less than intact state where they have particle sizes of from 0.1 mm to 3 mm. Desirably, the nuts and oats, once powdered or crushed, can pass through a sieve having a sieve size of 1 mm, i.e. so that the particle size is 1 mm or less. For example, the powdered or crushed nuts/oats can be generally obtained by passing intact nuts/oats through a food processor, running through a sieve, and returning the un-passed material through the food processor again. The powdered or crushed nuts/oats generally have a consistency similar to that of a powder or soft sand.

Depending on the degree of abrasiveness desired in the scrub bar, the amount of nuts and oats will vary. Generally, the nuts and oats are present in a weight ratio of about 1:1 nuts:oats. Generally, the greater the amount of nuts and oats, the more abrasive the scrub bar will be. In specific embodiments, the nuts comprise about 6.25 weight percent of the scrub bar and the oats comprise about 6.25 weight percent of the scrub bar. In other embodiments, the nuts comprise about 9.375 weight percent of the scrub bar and the oats comprise about 9.375 weight percent of the scrub bar. In still other embodiments, the nuts comprise about 10 weight percent of the scrub bar and the oats comprise about 10 weight percent of the scrub bar. The nuts and oats provide an abrasive surface for effective exfoliation, but are gentle to the skin, unlike harsh pumice.

The glycerin serves as a base in which the nuts and oats are dispersed. The glycerin may comprise from about 75 to about 88 weight percent of the scrub bar. As used here, the term "glycerin" does not refer to the specific chemical compound also known as glycerol(1,2,3-propanetriol). Instead, the term "glycerin" refers to the common soap base generally formed from the reaction of a fat and lye, which can contain ~7-20% pure glycerol.

Desirably, the scrub bar contains natural ingredients. In particular, the scrub bar does not contain animal fats or oils, methyl alcohol or ethyl alcohol, colorants, or odorants in specific embodiments.

The oats and nuts may be evenly dispersed throughout the glycerin. In some embodiments, the oats and nuts are preferentially located near a surface of the scrub bar. Put another way, a majority (by weight) of the oats and nuts in the scrub bar are dispersed close to a surface of the scrub bar (rather than within the internal volume of the bar). The dispersion of the oats and nuts within the glycerin can be controlled by methods known in the art.

The scrub bar of the present disclosure can be made using methods known in the art. For example, the nuts and oats may be pulverized or powdered using devices such as a food processor. The degree of powdering can be controlled, for example, by using a sieve to obtain the desired powder size. Next the glycerin is provided in a liquid form, for example, by melting a solid glycerin base. The powdered or crushed nuts/oats are then added to the liquid glycerin. The liquid glycerin can be mixed, for example, by stirring, to disperse the nuts and oats within the glycerin. The degree of dispersion can be controlled by the amount of stirring. The mixture of glycerin, nuts, and oats can then be poured into a mold. The mold is then cooled to harden the scrub bar. Cooling is generally passive, in other words, the mold is simply left at room temperature until the liquid mixture has been cooled and hardens. If desired, active cooling, such as with water or air, may be used as well. The scrub bar is then removed from the mold by turning the mold upside down.

Exemplary embodiments include a soap bar containing 0.5 ounces of a nut/oat mixture with 3.5 ounces of glycerin; a soap bar containing 0.75 ounces of a nut/oat mixture with 3.25 ounces of glycerin; and a soap bar containing 0.75 ounces of a nut/oat mixture with 3 ounces of glycerin.

Although particular embodiments have been described, alternatives, modifications, variations, improvements, and substantial equivalents that are or may be presently unforeseen may arise to applicants or others skilled in the art. Accordingly, the claims as filed or as they may be amended are intended to embrace all such alternatives, modifications, variations, improvements, and substantial equivalents.

Figure 1:
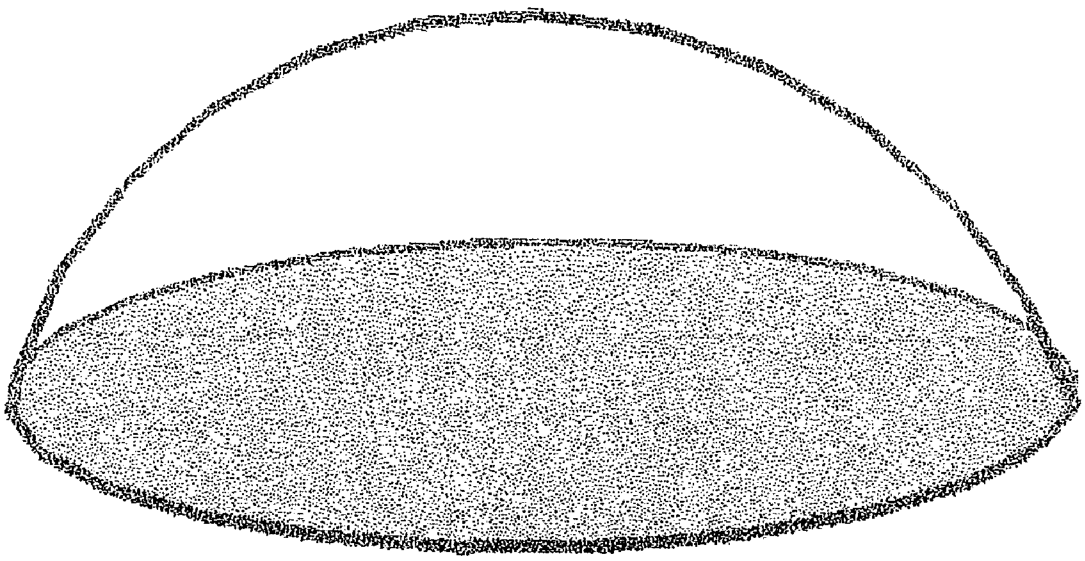
FIG. 1 is a tilted side view that shows the top and bottom of the exfoliating scrub bar of the present invention.

The invention claimed is:

1. A scrub bar consisting of:

from about 6 to about 12.5 weight percent of powdered or crushed nuts selected from the group consisting of almonds, walnuts, pecans, cashews, macadamia and pistachios;

from about 6 to about 12.5 weight percent of powdered or crushed oats;

from about 75 to about 88 weight percent of soap base; and wherein the weight ratio of nuts to oats is about 1:1.

2. A method for producing a scrub bar, the method consisting of:

providing liquid soap base in a container;

adding powdered or crushed nuts selected from the group consisting of almonds, walnuts, pecans, cashews, macadamia and pistachios to the liquid soap base;

adding powdered or crushed oats to the liquid soap base;

mixing the liquid soap base to disperse the nuts and oats, thereby forming a mixture;

pouring the mixture into a mold; and cooling the mixture to form the scrub bar.

3. The scrub bar of claim 1, wherein the nuts comprise about 6.25 weight percent of the scrub bar and the oats comprise about 6.25 weight percent of the scrub bar.

4. The scrub bar of claim 1, wherein the nuts comprise about 9.375 weight percent of the scrub bar and the oats comprise about 9.375 weight percent of the scrub bar.

5. The scrub bar of claim 1, wherein the nuts comprise about 10 weight percent of the scrub bar and the oats comprise about 10 weight percent of the scrub bar.

6. The scrub bar of claim 1, wherein the nuts and oats have a particle size of 1 mm or less.

7. The scrub bar of claim 1, wherein the oats and nuts are evenly dispersed throughout the glycerin.

8. The scrub bar of claim 1, wherein the oats and nuts are preferentially located near a surface of the scrub bar.

* * * * *